US009381150B2

(12) United States Patent
Cunningham et al.

(10) Patent No.: US 9,381,150 B2
(45) Date of Patent: Jul. 5, 2016

(54) ALCOHOL ANTIMICROBIAL SKIN SANITIZING COMPOSITIONS INCLUDING CATIONIC COMPATIBLE THICKENERS

(75) Inventors: Corey Thomas Cunningham, Larsen, WI (US); Jeffery Richard Seidling, Neenah, WI (US); Scott W. Wenzel, Neenah, WI (US); Stacy Averic Mundschau, Weyauwega, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1690 days.

(21) Appl. No.: 12/044,550

(22) Filed: Mar. 7, 2008

(65) Prior Publication Data

US 2009/0226497 A1 Sep. 10, 2009

(51) Int. Cl.

| A01N 25/08 | (2006.01) |
| A61K 8/86 | (2006.01) |
| A01N 31/02 | (2006.01) |
| A61K 8/34 | (2006.01) |
| A61K 8/39 | (2006.01) |
| A61K 8/41 | (2006.01) |
| A61K 8/81 | (2006.01) |
| A61Q 17/00 | (2006.01) |

(52) U.S. Cl.
CPC . *A61K 8/86* (2013.01); *A01N 31/02* (2013.01); *A61K 8/34* (2013.01); *A61K 8/39* (2013.01); *A61K 8/416* (2013.01); *A61K 8/8158* (2013.01); *A61K 8/8182* (2013.01); *A61Q 17/005* (2013.01)

(58) Field of Classification Search
CPC ....... A01N 31/02; A01N 25/04; A01N 33/12; A01N 47/44; A01N 49/00; A01Q 17/005; A01Q 19/10; A61K 8/31; A61K 8/34; A61K 2800/28; A61K 8/0204; A61K 8/0241; A61K 8/042
See application file for complete search history.

(56) References Cited

U.S. PATENT DOCUMENTS

| 4,667,890 A | 5/1987 | Gietman, Jr. |
| 4,999,047 A | 3/1991 | Schuppiser |
| 5,288,486 A | 2/1994 | White |
| 5,540,332 A | 7/1996 | Kopacz et al. |
| 5,997,893 A | 12/1999 | Jampani et al. |
| 6,022,551 A | 2/2000 | Jampani et al. |
| 6,090,395 A | 7/2000 | Asmus et al. |
| 6,352,701 B1 | 3/2002 | Scholz et al. |
| 6,423,329 B1 | 7/2002 | Sine et al. |
| 6,651,924 B2 | 11/2003 | Gingras et al. |
| 6,723,689 B1 | 4/2004 | Hoang et al. |
| 6,846,846 B2 | 1/2005 | Modak et al. |
| 6,905,748 B2 | 6/2005 | Sosalla |
| 7,101,612 B2 | 9/2006 | Lang et al. |
| 7,268,165 B2 | 9/2007 | Greten et al. |
| 2005/0271595 A1 | 12/2005 | Brown |
| 2006/0204466 A1 | 9/2006 | Littau et al. |
| 2006/0281663 A1 | 12/2006 | Asmus |

FOREIGN PATENT DOCUMENTS

| EP | 0363748 A2 | 4/1990 |
| EP | 1281319 | 2/2003 |
| EP | 1820396 A1 | 8/2007 |
| WO | 9830095 A1 | 7/1998 |
| WO | WO 02/07701 | * 1/2002 | ............... A61K 7/50 |
| WO | 2004084973 A2 | 10/2004 |

OTHER PUBLICATIONS

International Search Report and Written Opinion regarding PCT/IB2009/050602, dated Sep. 15, 2009.
Paulson, D.S., et al., "A close look at alcohol gel as an antimicrobial sanitizing agent." American Journal of Infection Control, 1999, vol. 27, No. 4, pp. 332-338.
CFTA, International Cosmetic Ingredient Dictionary and Handbook, 11th Edition (2006); pp. 2154-2158.
2007 Cosmetic Bench Reference, www.CosmeticBenchReference.com; (hard copy provided from 2006 Cosmetic Bench Reference, pp. 652-653; 691-692; 741-742).
Office action received in Mexican Patent Application No. MX/a/2010/009839, dated Dec. 1, 2011.
Letter from associate regarding rejections in Office action received in Mexican Patent Application No. MX/a/2010/009839, dated Dec. 1, 2011.
Second Office Action for Patent Application Serial No. 200980108019.5 dated Jul. 18, 2012; 5 pages.
Letter from associate regarding rejections in second Office action received in Mexican Patent Application No. MX/a/20101009839, dated Jun. 21, 2012.
Extended European Search Report for EP Patent Application No. 09717111.0 mailed May 7, 2013.

* cited by examiner

*Primary Examiner* — Nannette Holloman
(74) *Attorney, Agent, or Firm* — Armstrong Teasdale LLP

(57) ABSTRACT

The present disclosure generally relates to alcohol antimicrobial skin sanitizing compositions for use in hand washing and skin sanitizing. The antimicrobial skin sanitizing composition comprises an alcohol for providing effective antimicrobial control, one or more cationic compounds for moisturizing and protecting the skin, and a compatible thickening system for thickening the antimicrobial skin sanitizing composition. The antimicrobial skin sanitizing compositions can be used alone or in combination with personal care products.

20 Claims, No Drawings

ALCOHOL ANTIMICROBIAL SKIN SANITIZING COMPOSITIONS INCLUDING CATIONIC COMPATIBLE THICKENERS

BACKGROUND OF DISCLOSURE

The present disclosure generally relates to antimicrobial skin sanitizing compositions including alcohols that are effective in killing microorganisms without damaging the user's skin. More particularly, the alcohol antimicrobial skin sanitizing compositions include cationic compounds for conditioning the skin and thickening systems that are compatible with the cationic compounds.

Hand washing is an essential component of infection control activities for consumers. Hand washing procedures are performed in several ways. Several procedures include an ordinary antimicrobial bar soap, a skin disinfecting alcohol based preparation agent, or alcohol instant hand sanitizer. Although alcohol and alcohol-containing compositions are known to possess bactericidal activity and to prevent nosocomial infections in hospital settings between patients, nurses and doctors, the compliance of using alcohol-based compositions is declining due to their inherent dehydrating and/or defatting properties, caused by the denaturing of proteins and removing of lipids from the skin. As such, continuous use of such products can leave the user's skin dry, often developing red, chapped and cracked skin.

To improve a user's skin, many companies have conventionally included humectants, emollients, and the like as additional components in their skin sanitizing alcohol-based compositions. While lending some protection, standard humectants and emollients are not long-lasting. As such, while providing minimal damage protection, the compositions break down and again begin to damage the user's skin, causing the user to discontinue use of the composition for sanitization.

One additional class of compounds that has been found to be highly effective at providing substantive and long lasting conditioning effects to the skin, are cationic compounds such as quaternary ammonium compounds. Furthermore, it has been found that quaternary ammonium compounds aid in the deposition of humectants onto the skin, which can further help moisturize the skin. While good at conditioning, however, these compounds are incompatible with conventionally used hydroalcoholic thickening systems such as those used in the alcohol-based compositions. Thickening systems are conventionally used to adjust the viscosity and/or stability of the compositions. For example, conventional thickeners for use in the alcohol-based compositions for modifying viscosity and stability include cellulose polymers (e.g., hydroxypropylcellulose) and polyacrylates (e.g., carbomers).

The present disclosure addresses these problems by providing alcohol antimicrobial skin sanitizing compositions including thickening systems that may be used in combination with cationic compounds, such as quaternary ammonium compounds. The alcohol antimicrobial skin sanitizing composition comprises a combination of an alcohol, thickeners and cationic compounds that together have efficacy against a broad spectrum of microorganisms, while preventing drying and cracking of the skin upon use.

SUMMARY OF THE DISCLOSURE

The present disclosure generally relates to an alcohol antimicrobial skin sanitizing composition for use in hand washing and skin sanitizing. The alcohol antimicrobial skin sanitizing composition comprises an alcohol for providing effective antimicrobial control, one or more cationic compounds for moisturizing, conditioning, and protecting the skin, and a compatible thickening system for thickening the composition.

In one aspect, the present disclosure is directed to an antimicrobial skin sanitizing composition comprising: an alcohol; a cationic compound for imparting a skin conditioning benefit to a user; and a thickening system compatible with the cationic compound. The thickening system is essentially free of a cellulosic polymer, starch, acrylates, and acrylate-based polymers.

In another aspect, the present disclosure is further directed to an antimicrobial skin sanitizing composition comprising an alcohol; a cationic compound for imparting a skin conditioning benefit to a user; and a thickening system compatible with the cationic compound. The thickening system of this embodiment comprises a thickener selected from the group consisting of PEG-150 stearate, PEG-150 distearate, PEG-175 diisostearate, polyglyceryl-10 behenate/eicosadioate, disteareth-100 IPDI, polyacrylamidomethylpropane sulfonic acid, butylated PVP, and combinations thereof.

Other objects and features will be in part apparent and in part pointed out hereinafter.

DETAILED DESCRIPTION OF THE DISCLOSURE

The present disclosure generally relates to an antimicrobial skin sanitizing composition for use in hand washing and skin sanitizing. The antimicrobial skin sanitizing compositions include both alcohols that are effective in killing microorganisms and cationic compounds for conditioning the skin so as to cleanse and/or disinfect the user's skin without causing damage. It should be recognized that "sanitizing compositions" can refer to compositions that either cleanse/remove antimicrobials on the skin without damaging and/or killing the antimicrobials, or kill the antimicrobials (i.e., disinfect) and still be within the scope of the present disclosure. The antimicrobial skin sanitizing compositions further include thickening systems that are compatible with the cationic compounds for adjusting the viscosity of the compositions.

In accordance with the present disclosure, it has been discovered that thickening systems including one or more various thickeners can be used in combination with cationic conditioners and skin-benefit compounds within an alcohol-based antimicrobial skin sanitizing composition for providing microbiocidal efficacy without damaging the skin of the user. In one particular embodiment, the combination of an alcohol, quaternary ammonium salt, and compatible thickening system has been found to be an effective microbicide for a broad spectrum of bacteria and fungi, while conditioning and protecting the user's skin. As used herein, the term "compatible" refers to a compound that, when mixed with the cationic compound, does not separate out a white or cloudy coacervate and, in some embodiments, the compatible compound prevents phase separation of the cationic-anionic complex as discontinuous liquid droplets in the continuous hydroalcoholic phase. Furthermore, a compatible thickening system will allow the user to perceive the desired skin conditioning effect intended by the cationic compound when mixed with the thickening system; that is, the cationic compound will not be bound to the thickening system, thereby preventing the cationic compound from providing its desired effect. The term "microbiocide" refers to a compound capable of killing, inhibiting the growth of, or controlling the growth of microorganisms. Biocides include bactericides, fungicides, and algaecides. The term "microorganism" includes, for example, fungi (including yeast and mold), bacteria, and algae.

Thus, in one aspect, the present disclosure is directed to an antimicrobial skin sanitizing composition including an alcohol, a thickening system, and a cationic compound. The antimicrobial skin sanitizing composition may be formulated with a suitable pharmaceutically acceptable carrier into compositions such as gels, lotions, creams, liquids, and the like, that may be applied to skin or mucosa. For example, in one particularly preferred embodiment, the antimicrobial skin sanitizing composition is suitable in the form of an instant hand sanitizer.

In another aspect, an antimicrobial skin sanitizing composition of the present disclosure may be used in combination with a product, such as a personal care product. More particularly, the antimicrobial skin sanitizing composition may be incorporated into or onto a substrate, such as a wipe substrate, an absorbent substrate, a fabric or cloth substrate, or a tissue substrate, among others. For example, the antimicrobial skin sanitizing compositions may be incorporated into personal care products, such as wipes, absorbent articles, bath tissues, cloths, and the like. In one preferred embodiment, the antimicrobial skin sanitizing composition is a liquid composition that may be used in combination with a wipe substrate to form a wet wipe.

The presence of the alcohol in the antimicrobial skin sanitizing compositions provides the compositions with microbicidal properties against most bacteria and fungi. More particularly, the alcohol is suitably capable of killing gram-positive, gram-negative bacteria, fungi, parasites, and a variety of viruses. The potent activity of the alcohol against a microorganism is due to its denaturation of proteins and enzymes and cellular dehydration.

Suitable alcohols for use within the antimicrobial skin sanitizing composition can include any water-soluble alcohol known in the art. Specific examples of suitable alcohols include, for example, methyl alcohol, ethyl alcohol, iso-propyl alcohol, n-propyl alcohol, n-butyl alcohol, t-butyl alcohol, iso-butyl alcohol, and combinations thereof.

Typically, the more concentrated the alcohol-containing composition, the more potent the antimicrobial effect. However, increasing the alcohol concentration has the deleterious effect of increasing the level of skin irritancy on users of the composition. Suitably, the present disclosure describes an antimicrobial skin sanitizing composition with an alcohol concentration of at least 60% (by weight). More suitably, the antimicrobial skin sanitizing composition includes from about 60% (by weight) to about 99.98% (by weight) alcohol, even more suitably, from about 60% (by weight) to about 80% (by weight) and, even more suitably, about 70% (by weight) alcohol.

As noted above, the alcohol present in the antimicrobial skin sanitizing compositions can cause irritation to the skin of the user, such as chapping and cracking, thereby causing the user to discontinue use of the compositions. To help condition and protect the user's skin, the antimicrobial skin sanitizing compositions of the present disclosure further includes one or more cationic compounds capable of imparting a skin conditioning benefit or other skin benefit to the user.

Any suitable cationic compounds known in the art for conditioning the skin may be used in the antimicrobial skin sanitizing compositions of the present disclosure. Particularly preferred cationic compounds can include, for example, quaternium salts, polyquaterniums, quaterniums, quaternium hectorites (e.g., Quaternium-18 hectorite), cationic surfactants, cationic silicones, and combination thereof. As used herein, "quaternium salts" refers to a solid, or semi-solid, compound at room temperature that contains at least one discrete cationic charge and at least one appropriate anion. One particular example of a quaternium salt is benzalkonium chloride. One particularly preferred cationic compound for use in the present antimicrobial skin sanitizing composition is a quaternary ammonium compound, such as a quaternary ammonium salt.

Suitable polyquaterniums for use in the antimicrobial skin sanitizing compositions include Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-21, Polyquaternium-22, Polyquaternium-23, Polyquaternium-24, Polyquaternium-25, Polyquaternium-26, Polyquaternium-27, Polyquaternium-28, Polyquaternium-30, Polyquaternium-31, Polyquaternium-32, Polyquaternium-33, Polyquaternium-34, Polyquaternium-35, Polyquaternium-36, Polyquaternium-37, Polyquaternium-38, Polyquaternium-39, Polyquaternium-40, Polyquaternium-41, Polyquaternium-42, Polyquaternium-43, Polyquaternium-44, Polyquaternium-45, Polyquaternium-46, Polyquaternium-47, Polyquaternium-48, Polyquaternium-49, Polyquaternium-50, Polyquaternium-51, Polyquaternium-52, Polyquaternium-53, Polyquaternium-54, Polyquaternium-55, Polyquaternium-56, Polyquaternium-57, Polyquaternium-58, Polyquaternium-59, Polyquaternium-60, Polyquaternium-61, Polyquaternium-62, Polyquaternium-63, Polyquaternium-64, Polyquaternium-65, Polyquaternium-66, Polyquaternium-67, Polyquaternium-68, Polyquaternium-69, Polyquaternium-70, Polyquaternium-71, Polyquaternium-72, Polyquaternium-73, Polyquaternium-74, Polyquaternium-75, and Polyquaternium-76. Particularly preferred polyquateriums include Polyquaternium-2 (available as Miracare A-15 from Rhodia, Inc., Cranbury, N.J.); Polyquaternium-7 (available as Mackernium 007 from McIntyre Group, Ltd., University Park, Ill.); Polyquaternium-29 (available as Merquate 3330, 3331, 3333, and 3940 from Nalco Company, Naperville, Ill.); and Polyquaternium-44 (available as Luviquat UltraCare, BASF Corporation, Florham Park, N.J.).

Suitable quaterniums include Quaternium-8, Quaternium-14, Quaternium-15, Quaternium-16, and Quaternium-18.

Suitable cationic surfactants for use in the antimicrobial skin sanitizing compositions of the present disclosure include, for example, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include palmitamidopropyltrimonium chloride, centrimonium chloride, behentrimonium methosulfate, behenyltrimonium chloride, stearalkonium chloride, distearalkonium chloride, distearyldimonium chloride, chlorohexidine diglutamate, polyhexamethylene biguanide (PHMB), cetyl pyridinium chloride, benzammonium chloride, benzalkonium chloride, and combinations thereof.

Other suitable cationic compounds for use in the skin sanitizing compositions of the present disclosure include those cationic compounds listed in International Cosmetic Ingredient Dictionary and Handbook, 11$^{th}$ Edition (2006) and in 2007 Cosmetic Bench Reference, available on-line at http:// www.CosmeticBenchReference.com, both of which are incorporated by reference herein to the extent they are consistent herewith.

The antimicrobial skin sanitizing compositions of the present disclosure can typically include from about 0.01% (by weight) to about 10% (by weight) cationic compound. More suitably, the compositions can include from about 0.1% (by weight) to about 5% (by weight) cationic compound.

In addition to the alcohol and cationic compound, a thickening system is used in the antimicrobial skin sanitizing compositions to adjust the viscosity and stability of the compositions. Specifically, thickening systems are desirable to prevent the composition from running off of the hands or body during dispensing and use of the composition. When the sanitizing composition is used with a wipe product, a thicker formulation is desired to prevent the composition from migrating from the wipe substrate. Furthermore, by increasing the viscosity of the composition, evaporation of the alcohol within the composition is slowed, allowing for more contact time between the alcohol and microorganisms.

Conventionally used thickening systems, however, have been found incompatible with the above cationic compounds. Particularly, antimicrobial skin sanitizing compositions made using thickening systems including cellulosic polymers, starches, acrylates, and/or acrylate-based polymers, and having cationic compounds made in the past have had problems with separating out a white or cloudy coacervate and/or phase separation. This can be aesthetically unpleasing, which can dissuade the user from buying and using the composition. Furthermore, thickening systems of these previous antimicrobial skin sanitizing compositions include thickeners that can bind the cationic compounds, preventing the cationic compound from providing its intended benefit (e.g., conditioning benefit such as a moisturizing or lubricating benefit) to the skin of the user. Specifically, users of the antimicrobial skin sanitizing compositions have been unable to perceive the skin conditioning effects of the cationic compounds used in conventional antimicrobial skin sanitizing compositions. As such, the thickening systems used in the compositions of the present disclosure are essentially free of cellulosic polymers, starches, acrylates, and acrylate-based polymers. As used herein, the term "essentially free" refers to a thickening system that includes a cellulosic, starch, acrylate, and/or acrylate-based polymer in trace amounts or less. Furthermore, "acrylates and acrylate-based polymers" refers to polyacrylic acid-based polymers, polyacrylic acid ester-based polymers, and copolymers or crosspolymers of one or more monomers of acrylic aid, methyacrylic acid, or one of their simple esters. Not included, however, are polyacrylamides, which can be used in the instant disclosure as a thickener.

Generally, due to the use of alcohol as a solvent, the typical thickening system includes one or more thickeners that remain soluble in alcohol concentrations up to at least 70%. Furthermore, as noted above, the thickening system should be compatible with the cationic compounds used in the present disclosure; that is, the thickening system, when used in combination with one or more cationic compounds, should not precipitate out a coacervate or prevent the user from perceiving the conditioning benefit (or other desired benefit) to be gained from the cationic compound. Alternatively, the thickening system can include a cationically-charged thickener, which can provide both the thickening effect desired from the thickening system and a conditioning effect to the user's skin.

Preferable thickeners for use in the thickening system can include, for example, PEG-150 stearate, PEG-150 distearate, PEG-175 diisostearate, polyglyceryl-10 behenate/eicosadioate, disteareth-100 IPDI, polyacrylamidomethylpropane sulfonic acid, butylated PVP, and combinations thereof.

While the viscosity of the composition will typically depend on the thickener used and the other components of the composition, the thickeners of the composition suitably provide for a composition having a viscosity in the range of greater than 10 cP to about 30,000 cP or more. More preferably, the thickeners provide a composition having a viscosity of from about 100 cP to about 12,000 cP.

Typically, the antimicrobial skin sanitizing compositions of the present disclosure include the thickening system in an amount of no more than about 40% (by weight), and more suitably, from about 0.01% (by weight) to about 40% (by weight). More suitably, the thickening system is present in the antimicrobial skin sanitizing composition in an amount of from about 0.05% (by weight) to about 35% (by weight), even more suitably, from about 0.1% (by weight) to about 20% (by weight), and even more suitably, from about 0.2% (by weight) to about 10% (by weight).

As noted above, the antimicrobial skin sanitizing compositions of the present disclosure may be formulated with one or more conventional pharmaceutically-acceptable and compatible carrier materials. The antimicrobial skin sanitizing composition may take a variety of forms including, without limitation, aqueous solutions, gels, balms, lotions, suspensions, creams, milks, salves, ointments, sprays, emulsions, oils, resins, foams, solid sticks, aerosols, and the like. Carrier materials suitable for use in the instant disclosure include those well-known for use in the cosmetic and medical arts as a basis for ointments, lotions, creams, salves, aerosols, gels, suspensions, sprays, foams, and the like, and may be used in their art-established levels.

Non-limiting examples of suitable carrier materials include water, emollients, humectants, natural and synthetic fats or oils, polyols, surfactants, alcohols, esters, silicones, clays, and other pharmaceutically acceptable carrier materials. As will be recognized by one skilled in the art, the relative amounts of components in the compositions of the disclosure that can be used to formulate the composition will be dictated by the nature of the composition. The levels can be determined by routine experimentation in view of the disclosure provided herein.

Thus, in one embodiment, the antimicrobial skin sanitizing composition of the disclosure can optionally include one or more emollients, which typically acts to soften, soothe, and otherwise lubricate and/or moisturize the skin. Suitable emollients that can be incorporated into the compositions include oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof.

Without being limiting, the esters can be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients. Other suitable ester compounds for use in the hand sanitizing compositions or the present disclosure are listed in International Cosmetic Ingredient Dictionary and Handbook, 11th Edition (2006) and in 2007 Cosmetic Bench Reference, available on-line at http://www.CosmeticBenchReference.com, both of which are incorporated by reference herein to the extent they are consistent herewith.

The composition may desirably include one or more emollient in an amount of from about 0.01% (w/w) to about 20% (w/w), more desirably from about 0.05% (w/w) to about 10% (w/w), and even more desirably from about 0.10% (w/w) to about 5% (w/w).

Humectants that are suitable as carriers in the sanitizing composition of the present disclosure include, for example, glycerin, glycerin derivatives, sodium hyaluronate, betaine, amino acids, glycosaminoglycans, honey, sorbitol, glycols, polyols, sugars, hydrogenated starch hydrolysates, salts of PCA, lactic acid, lactates, urea, and the like, and combinations thereof. Particularly preferred humectants are glycerin, propylene glycol, butylene glycol, methyl gluceth-10, methyl gluceth-10, and sugar alcohols.

The composition of the disclosure can desirably include one or more humectants in an amount of from about 0.01% (w/w) to about 20% (w/w), more desirably from about 0.05% (w/w) to about 10% (w/w), and even more desirably from about 0.1% (w/w) to about 5.0% (w/w).

The compositions of the disclosure can also include natural fats and oils. As used herein, the term "natural fat or oil" is intended to include fats, oils, essential oils, essential fatty acids, non-essential fatty acids, phospholipids, and combinations thereof. These natural fats and oils can provide a source of essential and non-essential fatty acids to those found in the skin's natural barrier. Suitable natural fats or oils can include citrus oil, olive oil, avocado oil, apricot oil, babassu oil, borage oil, camellia oil, canola oil, castor oil, coconut oil, corn oil, cottonseed oil, emu oil, evening primrose oil, hydrogenated cottonseed oil, hydrogenated palm kernel oil, maleated soybean oil, meadowfoam oil, palm kernel oil, peanut oil, rapeseed oil, grapeseed oil, safflower oil, sphingolipids, seed almond oil, tall oil, lauric acid, palmitic acid, stearic acid, linoleic acid, stearyl alcohol, lauryl alcohol, myristyl alcohol, behenyl alcohol, rose hip oil, calendula oil, chamomile oil, eucalyptus oil, juniper oil, sandlewood oil, tea tree oil, sunflower oil, soybean oil, and combinations thereof.

The composition of the disclosure may desirably include fats and oils in an amount of from about 0.01% (w/w) to about 20% (w/w), more desirably from about 0.05% (w/w) to about 10% (w/w), and even more desirably from about 0.1% (w/w) to about 5% (w/w).

In one preferred embodiment, the antimicrobial skin sanitizing compositions may comprise water. For instance, where the antimicrobial skin sanitizing composition is a wetting composition, such as described below for use with a wet wipe, the composition will typically comprise water. The compositions can suitably comprise water in an amount of from about 0.1% (w/w) to about 37.23% (w/w), more preferably from about 0.5% (w/w) to about 25% (w/w), and still more preferably from about 1.0% (w/w) to about 20% (w/w).

The compositions of the present disclosure may additionally include adjunct ingredients conventionally found in pharmaceutical compositions in their art-established fashion and at their art-established levels. For example, the compositions may comprise additional compatible pharmaceutically active materials for combination therapy, such as additional antimicrobial agents, antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof. Other suitable additives that may be included in the compositions of the present disclosure include colorants, deodorants, fragrances, perfumes, emulsifiers, anti-foaming agents, lubricants, skin conditioning agents, skin protectants and skin benefit agents (e.g., aloe vera and laponite), solvents, solubilizing agents, suspending agents, wetting agents, preservatives, pH adjusting ingredients, chelators, propellants, dyes and/or pigments, and combinations thereof.

In another aspect, the antimicrobial skin sanitizing compositions of the present disclosure may be used in combination with a product, such as a personal care product. More particularly, the composition may be incorporated into or onto a substrate, such as a wipe substrate, an absorbent substrate, a fabric or cloth substrate, or a tissue substrate, among others. For example, the compositions may be incorporated into personal care products, such as wipes, absorbent articles, bath tissues, cloths, and the like. More particularly, the antimicrobial skin sanitizing composition may be incorporated into wipes such as wet wipes, hand wipes, face wipes, cosmetic wipes, and the like, or absorbent articles, such as diapers, training pants, adult incontinence products, feminine hygiene products, and the like, and combinations thereof. In one preferred embodiment, the antimicrobial skin sanitizing composition is a liquid composition that may be used in combination with a wipe substrate to form a wet wipe or may be a wetting composition for use in combination with a dispersible wet wipe. In another embodiment, the antimicrobial skin sanitizing composition can be used in combination with a wipe substrate, which is packaged together with one or more absorbent articles, such as diapers.

Although discussed primarily in terms of a wetting composition for use in a wet wipe, it should be understood that the antimicrobial skin sanitizing compositions described herein can also be used in combination with numerous other personal care products, such as those described above.

Thus, in one particularly preferred embodiment, the antimicrobial skin sanitizing composition is incorporated into a wetting composition for use in a wet wipe.

The wet wipe may comprise a nonwoven material that is wetted with an aqueous solution termed the "wetting composition," which may also comprise the antimicrobial skin sanitizing composition disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, melt blown, and solution spinning.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5-10 and a length of about 6-15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

Wetting Composition

The wetting composition for use in combination with the nonwoven materials may desirably comprise the antimicrobial skin sanitizing composition of the present disclosure. As noted above, the antimicrobial skin sanitizing composition has efficacy against a broad spectrum of microorganisms. As such, the antimicrobial wetting composition will help keep microbiological and fungal growth in the wet wipe at an acceptable level.

The wetting composition may include a variety of additives or components, including those disclosed in U.S. Pat. No. 7,101,612 to Lang, which is incorporated herein in its entirety. Possible additives may include, but are not limited to skin-care additives, odor control additives, wetting agents and/or cleaning agents; water, emollients, surfactants, fragrances, preservatives, chelating agents, pH buffers, or combinations thereof as are well known to those skilled in the art. Further, the wetting agent may also contain lotions, medicaments, and/or other antimicrobials.

Relative to the weight of the dry substrate, the wet wipe may desirably contain from about 10 percent to about 600 percent of the wetting composition by weight, more desirably from about 50 percent to about 500 percent of the wetting composition by weight, even more desirably from about 100 percent to about 400 percent of the wetting composition by weight, and especially more desirably from about 200 to 300 percent of the wetting composition.

Method of Making Wet Wipes

The wetting composition may be applied to the fibrous material by any known process. Suitable processes for applying the wetting composition include, but are not limited to printing, spraying, electrostatic spraying, the use of metered press rolls or impregnating. The amount of wetting composition may be metered and distributed uniformly onto the fibrous material or may be non-uniformly distributed onto the fibrous material.

For ease of application, the wetting composition may be applied to the fibrous material in combination with a solvent, as a solution or mixture. A variety of solvents may be used, including, for example, water, methanol, ethanol, acetone, or the like, with water being the preferred solvent. The amount of wetting composition in the solvent may vary, depending on a variety of factors, including the identity and physical characteristics of the fibrous material to which the wetting composition is being applied. Desirably, the mixture or solution of the wetting composition may contain up to about 50 percent by weight of wetting composition solids. More desirably, the wetting composition or mixture may contain from about 10 to 30 percent by weight of wetting composition solids. Even more desirably, the wetting composition or mixture may contain about 12 to 25 percent by weight wetting composition solids.

Once the wetting composition is applied to the fibrous material, drying, if necessary, may be achieved by any conventional means. Once dry, the nonwoven material may exhibit improved tensile strength when compared to the tensile strength of the untreated wet-laid or dry-laid fibrous material.

The finished wet wipes may be individually packaged, desirably in a folded condition, in a moisture proof envelope or packaged in containers holding any desired number of sheets in a water-tight package with a wetting composition applied to the wipe. Some example processes which can be used to manufacture folded wet wipes are described in U.S. Pat. Nos. 5,540,332 and 6,905,748, which are incorporated by reference herein to the extent they are consistent herewith. The finished wipes may also be packaged as a roll of separable sheets in a moisture-proof container holding any desired number of sheets on the roll with a wetting composition applied to the wipes. The roll can be coreless and either hollow or solid. Coreless rolls, including rolls with a hollow center or without a solid center, can be produced with known coreless roll winders, including those of SRP Industry, Inc. (San Jose, Calif.); Shimizu Manufacturing (Japan), and the devices disclosed in U.S. Pat. No. 4,667,890. The U.S. Pat. No. 6,651,924 also provides examples of a process for producing coreless rolls of wet wipes.

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

In this Example, various thickeners were added to hydroalcoholic compositions to determine their thickening capabilities.

To begin, three samples were prepared by adding 5% (by weight total hydroalcoholic composition) thickener to 32.5%

(by weight total hydroalcoholic composition) water and heated until the thickener melted and dispersed in the water (typically to a temperature of 60° C.). A fourth sample was prepared by adding 10% (by weight total hydroalcoholic composition) thickener to 27.5% (by weight total hydroalcoholic composition) water and heated until the thickener melted and dispersed in the water (typically to a temperature of 60° C.) The thickener/water mixture of all of the samples was then removed from heat and 62.5% (by weight total hydroalcoholic composition) ethanol was added to the mixture. The hydroalcoholic composition was mixed until cool.

The Brookfield viscosities of the samples were then measured using a Brookfield Viscometer II having either a S2 or S4 spindle and rotating at a speed of either 50 revolutions per minute (rpm) or 3 rpm. Specifically, varying spindles and speeds of the viscometer was necessary due to the limitations as to what each setting can accurately measure. The various thickeners, their commercial sources, amounts of thickeners, their Brookfield viscosities, and spindle/speed of viscometer used are shown in Table 1 below.

TABLE 1

| Thickener | Commercial Source | Amount (wt. %) | Viscosity (cP) | Spindle/Speed (rpm) |
|---|---|---|---|---|
| Polyglyceryl-10 Behenate/Eicosadioate | Nomcort HK-P (Nisshin OlliO Group, Ltd., Chuo-ku, Tokyo) | 10 | 2212 | S4/3 |
| PEG-150 Distearate | Rewopal PEG 6000DS (Rewo Chemische GmbH, Steinau, Germany) | 5 | 16.3 | S2/50 |
| PEG-175 Diisostearate | HEST HVB (Global Seven, Columbus, Ohio) | 5 | 17 | S2/50 |
| Disteareth-100 IPDI | Dermothix 100 (Alzo International, Inc., Sayreville, New Jersey) | 5 | 19.1 | S2/50 |

As shown in Table 1, one skilled in the art would recognize that the Polyglyceryl-10 Behenate/Eicosadioate system is much thicker than the remaining samples.

Example 2

In this Example, various thickeners were mixed with ethanol to evaluate their ability to thicken an anhydrous composition.

Specifically, three samples were prepared by adding 35% (by total weight composition) thickener to 65% (by total weight composition) ethanol. Two further samples were prepare by adding 17.5 (by total weight composition) thickener to 82.5% (by total weight composition) ethanol. A Brookfield Viscometer II, using various spindles at various speeds, was used to obtain the viscosity data of each composition. The various thickeners, their commercial sources, amounts of thickeners, the viscosity of the resulting composition of thickener and ethanol, and spindle and speed used to measure viscosity are shown in Table 2 below.

TABLE 2

| Thickener | Tradename and Commercial Supplier | Amount (wt. %) | Viscosity (cP) | Spindle/Speed (rpm) |
|---|---|---|---|---|
| Polyacrylamidomethylpropane sulfonic acid | Cosmedia HSP-1180 (Cognis Corporation, Care Chemicals, Ambler, Pennsylvania) | 35 | 9685 | S4/0.6 |
| Polyacrylamidomethylpropane sulfonic acid | Cosmedia HSP-1180 (Cognis Corporation, Care Chemicals, Ambler, Pennsylvania) | 35 | 11443 | 95/12 |
| Polyacrylamidomethylpropane sulfonic acid | Cosmedia HSP-1180 (Cognis Corporation, Care Chemicals, Ambler, Pennsylvania) | 17.5 | 1650 | S4/3 |
| Butylated PVP | Ganex P-904 (International Specialty Products, Wayne, New Jersey) | 35 | 403 | S4/6 |

TABLE 2-continued

| Thickener | Tradename and Commercial Supplier | Amount (wt. %) | Viscosity (cP) | Spindle/Speed (rpm) |
|---|---|---|---|---|
| Butylated PVP | Ganex P-904 (International Specialty Products, Wayne, New Jersey) | 17 | 93.7-105.9 | S3/10 |

Example 3

In this Example, various thickeners were mixed with ethanol and a polyquaternary ammonium compound to evaluate their ability to thicken the composition.

Specifically, the thickener was added to ethanol and 0.5% (by total weight composition) Polyquaternium-2 (commercially available as Mirapol A-15 from Rhodia Inc., Cranbury, N.J.) to form a composition. The example formulations were balanced with water, when necessary. A Brookfield Viscometer II was used to obtained the viscosity data of each composition. The various thickeners and the viscosity of the resulting composition of thickener and ethanol are shown in Table 3 below.

TABLE 3

| Thickener (Tradename and Commercial Supplier) | Thickener (wt %) | Ethanol (wt %) | Viscosity (cP) (Spindle/rpm) |
|---|---|---|---|
| Polyglyceryl-10 Behenate/Eicosadioate Nomcort HK-P, Nisshin Ollio Group, Ltd., Chuo-ku, Tokyo | 10.0 | 62.5 | 2631 (S4/3) |
| Butylated PVP (Ganex P-904 International Specialty Products, Wayne, New Jersey) | 35.0 | 64.5 | 434 (S4/6) |
| Butylated PVP (Ganex P-904 International Specialty Products, Wayne, New Jersey) | 17.5 | 82.0 | 86 (S3/10) |

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products without departing from the scope of the disclosure, it is intended that all matter contained in the above description shall be interpreted as illustrative and not in a limiting sense.

What is claimed is:

1. An antimicrobial skin sanitizing composition comprising:
   an alcohol;
   a cationic compound for imparting a skin conditioning benefit to a user; and
   a thickening system compatible with the cationic compound, wherein the thickening system is essentially free of cellulosic polymers, starches, acrylates, and acrylate-based polymers.

2. The antimicrobial skin sanitizing composition as set forth in claim 1 comprising at least about 60% by weight alcohol.

3. The antimicrobial skin sanitizing composition as set forth in claim 1 wherein the alcohol is selected from the group consisting of methyl alcohol, ethyl alcohol, iso-propyl alcohol, n-propyl alcohol, n-butyl alcohol, t-butyl alcohol, iso-butyl alcohol, and combinations thereof.

4. The antimicrobial skin sanitizing composition as set forth in claim 1 wherein the thickening system comprises a thickener selected from the group consisting of polyethylene glycol-150 distearate, polyethylene glycol-150 stearate, polyethylene glycol-175 diisostearate, polyglyceryl-10 behenate/eicosadioate, disteareth-100 IPDI, polyacrylamidomethylpropane sulfonic acid, butylated polyvinylpyrrolidone, and combinations thereof.

5. The antimicrobial skin sanitizing composition as set forth in claim 1 comprising no more than about 40% by weight thickening system.

6. The antimicrobial skin sanitizing composition as set forth in claim 1 wherein the cationic compound is selected from the group consisting of polyquaterniums, quaterniums, quaternium salts, quaternium hectorites, cationic surfactants, cationic silicones, and combinations thereof.

7. The antimicrobial skin sanitizing composition as set forth in claim 6 wherein the cationic compound is a quaternary ammonium compound.

8. The antimicrobial skin sanitizing composition as set forth in claim 1 comprising from about 0.01% by weight to about 10% by weight cationic compound.

9. The antimicrobial skin sanitizing composition as set forth in claim 1 further comprising an ingredient selected from the group consisting of emollients, humectants, natural fats and oils, anti-irritants, antimicrobial agents, antioxidants, anti-parasitic agents, antipuritics, antifungals, antiseptic actives, keratolytic actives, local anaesthetics, anti-stinging agents, anti-reddening agents, astringents, biological actives, deodorants, external analgesics, film formers, fragrances, skin condition agents, skin exfoliating agents, skin protectants, skin soothing, sunscreens, and combinations thereof.

10. An antimicrobial skin sanitizing composition comprising:
    an alcohol;
    a cationic compound for imparting a skin conditioning benefit to the user; and
    a thickening system comprising a thickener selected from the group consisting of polyethylene glycol-150 stearate, polyethylene glycol-150 distearate, polyethylene glycol-175 diisostearate, polyglyceryl-10 behenate/eicosadioate, disteareth-100 IPDI, polyacrylamidomethylpropane sulfonic acid, butylated polyvinylpyrrolidone, and combinations thereof, wherein the thickening system is compatible with the cationic compound and wherein the thickening system is essentially free of cellulosic polymers, starches, acrylates, and acrylate-based polymers.

11. The antimicrobial skin sanitizing composition as set forth in claim 10 wherein the alcohol is selected from the group consisting of methyl alcohol, ethyl alcohol, iso-propyl alcohol, n-propyl alcohol, n-butyl alcohol, t-butyl alcohol, iso-butyl, and combinations thereof.

12. The antimicrobial skin sanitizing composition as set forth in claim 10 comprising no more than about 40% by weight thickening system.

13. The antimicrobial skin sanitizing composition as set forth in claim 10 wherein the cationic compound is selected from the group consisting of polyquaterniums, quaterniums, quaternium salts, quaternium hectorites, cationic surfactants, cationic silicones, and combinations thereof.

14. The antimicrobial skin sanitizing composition as set forth in claim 10 further comprising an ingredient selected from the group consisting of emollients, humectants, natural fats and oils, anti-irritants, antimicrobial agents, antioxidants, anti-parasitic agents, antipuritics, antifungals, antiseptic actives, keratolytic actives, local anaesthetics, anti-stinging agents, anti-reddening agents, astringents, biological actives, deodorants, external analgesics, film formers, fragrances, skin condition agents, skin exfoliating agents, skin protectants, skin soothing, sunscreens, and combinations thereof.

15. A personal care product comprising:
a substrate; and
an antimicrobial skin sanitizing composition, the antimicrobial skin sanitizing composition comprising:
an alcohol;
a cationic compound for imparting a skin conditioning benefit to a user; and
a thickening system compatible with the cationic compound, wherein the thickening system is essentially free of cellulosic polymers, starches, acrylates, and acrylate-based polymers.

16. The personal care product as set forth in claim 15 wherein the alcohol is selected from the group consisting of methyl alcohol, ethyl alcohol, iso-propyl alcohol, n-propyl alcohol, n-butyl alcohol, t-butyl alcohol, iso-butyl alcohol, and combinations thereof.

17. The personal care product as set forth in claim 15 wherein the thickening system comprises a thickener selected from the group consisting of polyethylene glycol-150 stearate, polyethylene glycol-150 distearate, polyethylene glycol-175 diisostearate, polyglyceryl-10 behenate/eicosadioate, disteareth-100 IPDI, polyacrylamidomethylpropane sulfonic acid, butylated polyvinylpyrrolidone, and combinations thereof.

18. The personal care product as set forth in claim 15 wherein the cationic compound is selected from the group consisting of polyquaterniums, quaterniums, quaternium salts, quaternium hectorites, cationic surfactants, cationic silicones, and combinations thereof.

19. The personal care product as set forth in claim 15 being selected from the group consisting of wet wipes, hand wipes, face wipes, and cosmetic wipes.

20. The personal care product as set forth in claim 19 wherein the product is a wet wipe and the antimicrobial skin sanitizing composition is present in a wetting solution.

* * * * *